United States Patent
Hospodor et al.

(10) Patent No.: US 9,358,259 B2
(45) Date of Patent: Jun. 7, 2016

(54) RECYCLING CANNABINOID EXTRACTOR

(76) Inventors: Andrew David Hospodor, Santa Cruz, CA (US); Robert James Rapp, Lake Forest, CA (US)

(*) Notice: Subject to any disclaimer, the term of this patent is extended or adjusted under 35 U.S.C. 154(b) by 725 days.

(21) Appl. No.: 13/506,010

(22) Filed: Mar. 20, 2012

(65) Prior Publication Data

US 2013/0251824 A1    Sep. 26, 2013

(51) Int. Cl.
| | | |
|---|---|---|
| B01D 11/02 | (2006.01) |
| B06B 1/00 | (2006.01) |
| A61K 36/185 | (2006.01) |
| A61K 31/352 | (2006.01) |
| B06B 3/00 | (2006.01) |

(52) U.S. Cl.
CPC .......... *A61K 36/185* (2013.01); *B01D 11/0207* (2013.01); *B01D 11/0215* (2013.01); *B01D 11/0265* (2013.01); *A61K 31/352* (2013.01); *A61K 2236/30* (2013.01); *B01D 11/0288* (2013.01); *B06B 1/00* (2013.01); *B06B 3/00* (2013.01)

(58) Field of Classification Search
CPC ............... B01D 11/02; B01D 11/0265; B01D 11/0288; B01D 11/0219; A61K 31/352; A61K 36/60; A61K 2236/30; A61K 2236/53; B06B 3/00; B06B 1/20; B06B 1/00
USPC .................. 436/177, 178; 424/725; 210/209; 422/239, 261, 276, 277
See application file for complete search history.

(56) References Cited

U.S. PATENT DOCUMENTS

| | | | |
|---|---|---|---|
| 2,397,611 A | | 4/1946 | Lougovoy |
| 3,320,992 A | * | 5/1967 | Bodine .......................... 426/238 |
| 4,981,579 A | * | 1/1991 | Paspek et al. ................. 208/314 |
| 5,466,454 A | * | 11/1995 | Chang ........................... 424/725 |
| 5,700,464 A | * | 12/1997 | Silver ............................ 424/123 |
| 6,111,119 A | * | 8/2000 | Trout ............................... 554/16 |
| 6,365,416 B1 | | 4/2002 | Elsohly et al. |
| 6,730,519 B2 | | 5/2004 | Elsohly et al. |
| 7,344,736 B2 | | 3/2008 | Whittle et al. |
| 7,524,881 B2 | | 4/2009 | Goodwin et al. |

(Continued)

FOREIGN PATENT DOCUMENTS

WO   WO 2011/022938   * 3/2011

OTHER PUBLICATIONS

Benjamin De Backer et al, Journal of Chromatography B 877, Innovative development and validation ... determination of cannabinoids in cannabis ... 2009, pp. 4115-4124.

(Continued)

*Primary Examiner* — Katherine Zalasky
(74) *Attorney, Agent, or Firm* — Robert J. Rapp

(57) ABSTRACT

A process and apparatus for extracting cannabinoids from *cannabis* plant material plant material and for transporting low concentrations of cannabinoids in a solution of solvent includes at least a solvent tank, a hopper, and one or more pumps. A plurality of valves may also be incorporated into the invention. Plant material may be soaked, washed, and/or rinsed with a solvent that extracts essential elements from *cannabis* plant matter. The process minimally includes filling a hopper with plant mater, moving solvent from a solvent tank to the hopper, and moving solvent back to the solvent tank after an extraction. Repeating this process a plurality of times with new plant material increases the concentration cannabinoids in the solvent tank after each time the process is performed.

17 Claims, 5 Drawing Sheets

High Flow

(56) References Cited

U.S. PATENT DOCUMENTS

| | | |
|---|---|---|
| 7,592,468 B2 | 9/2009 | Goodwin et al. |
| 7,622,140 B2 | 11/2009 | Whittle et al. |
| 7,700,368 B2 * | 4/2010 | Flockhart et al. ............. 436/177 |
| 2002/0039795 A1 | 4/2002 | Elsohly et al. |
| 2003/0017216 A1 * | 1/2003 | Schmidt et al. ............... 424/725 |
| 2005/0165088 A1 | 7/2005 | Whittle et al. |
| 2008/0167483 A1 | 7/2008 | Whittle et al. |
| 2010/0119606 A1 | 5/2010 | Whittle et al. |
| 2011/0110723 A1 * | 5/2011 | Varma et al. ............. 405/128.75 |
| 2012/0251642 A1 * | 10/2012 | Gu et al. ........................ 424/757 |
| 2012/0263804 A1 * | 10/2012 | Hospodor .................... 424/725 |

OTHER PUBLICATIONS

Guo et al, The Application of Ultrasonic Degumming of Hemp, May 2010, China.

* cited by examiner

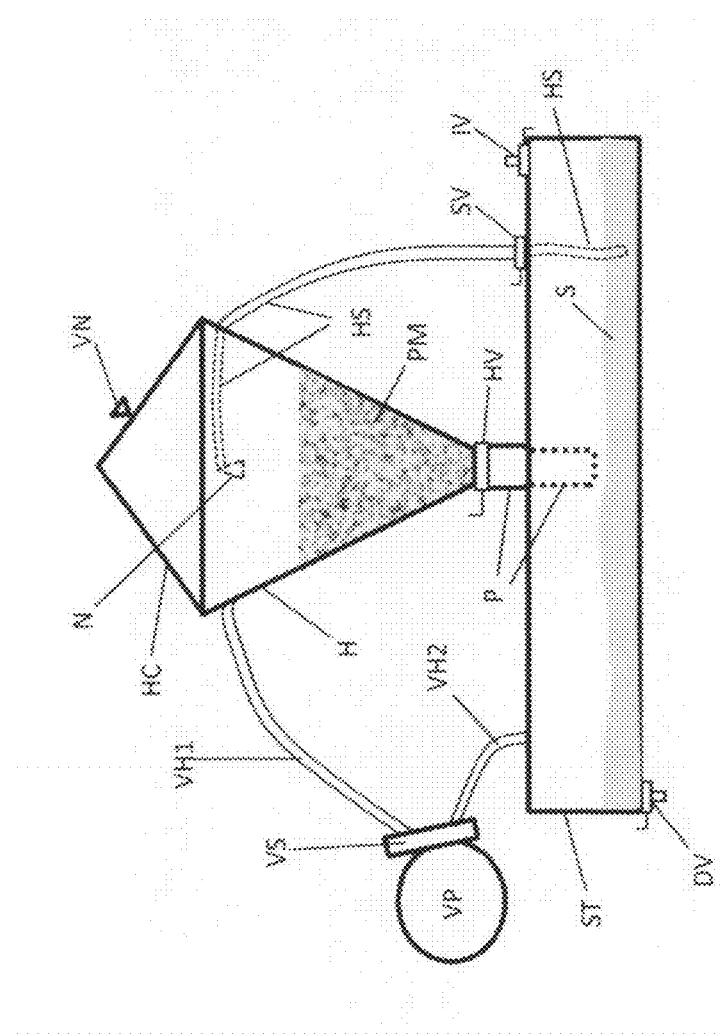

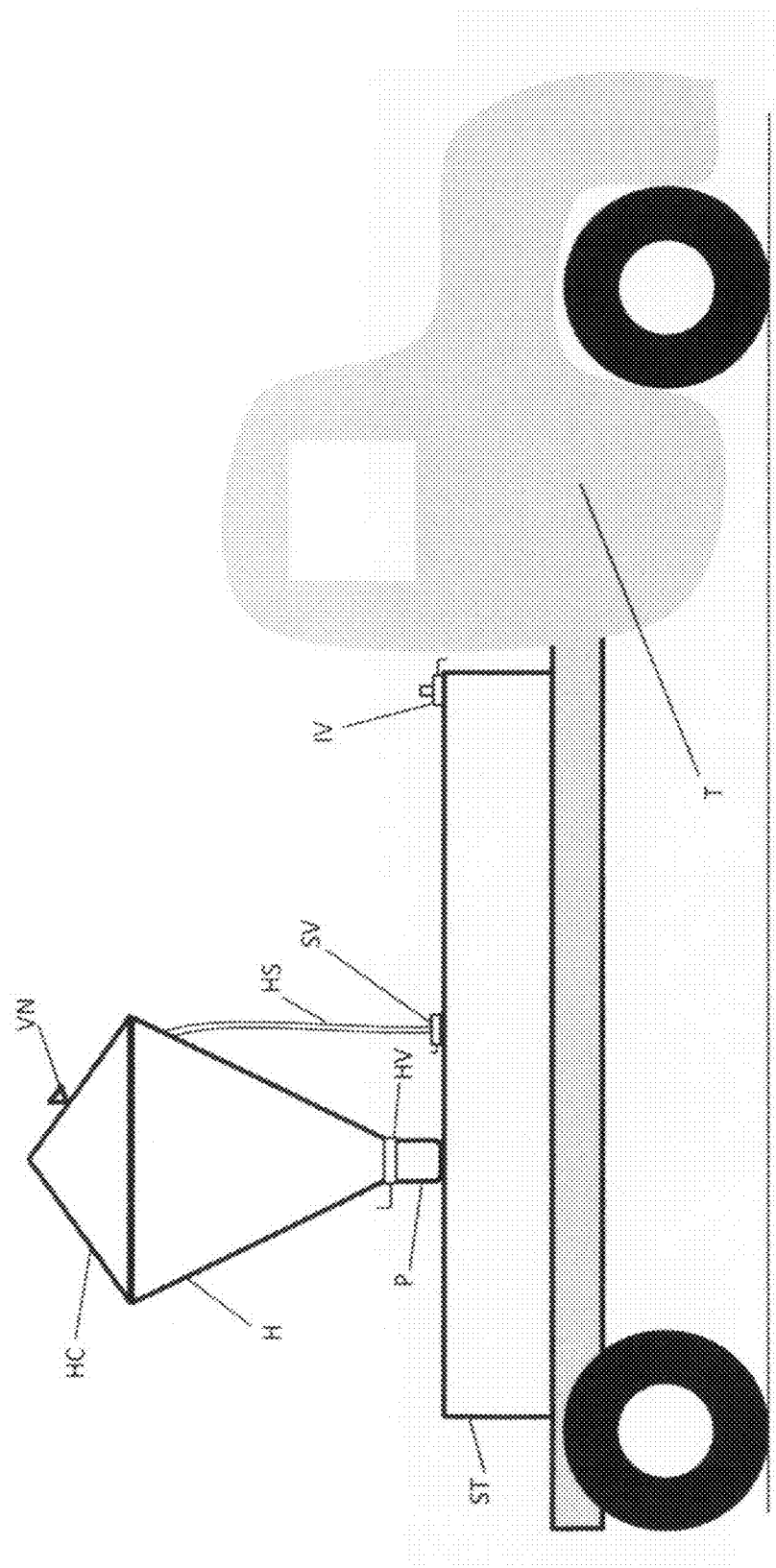
Figure 2: A Mobile Extractor Mounted on a Truck

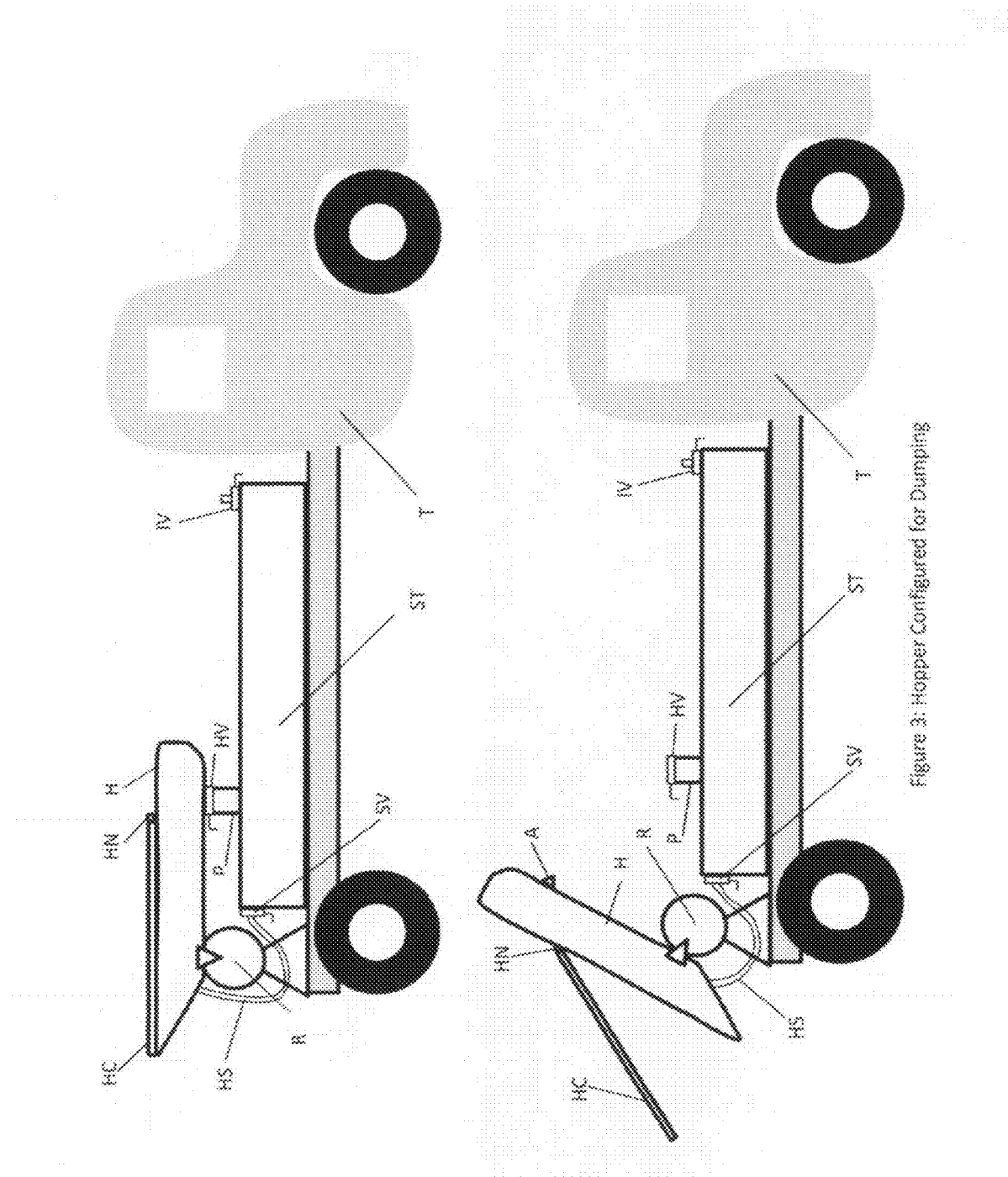

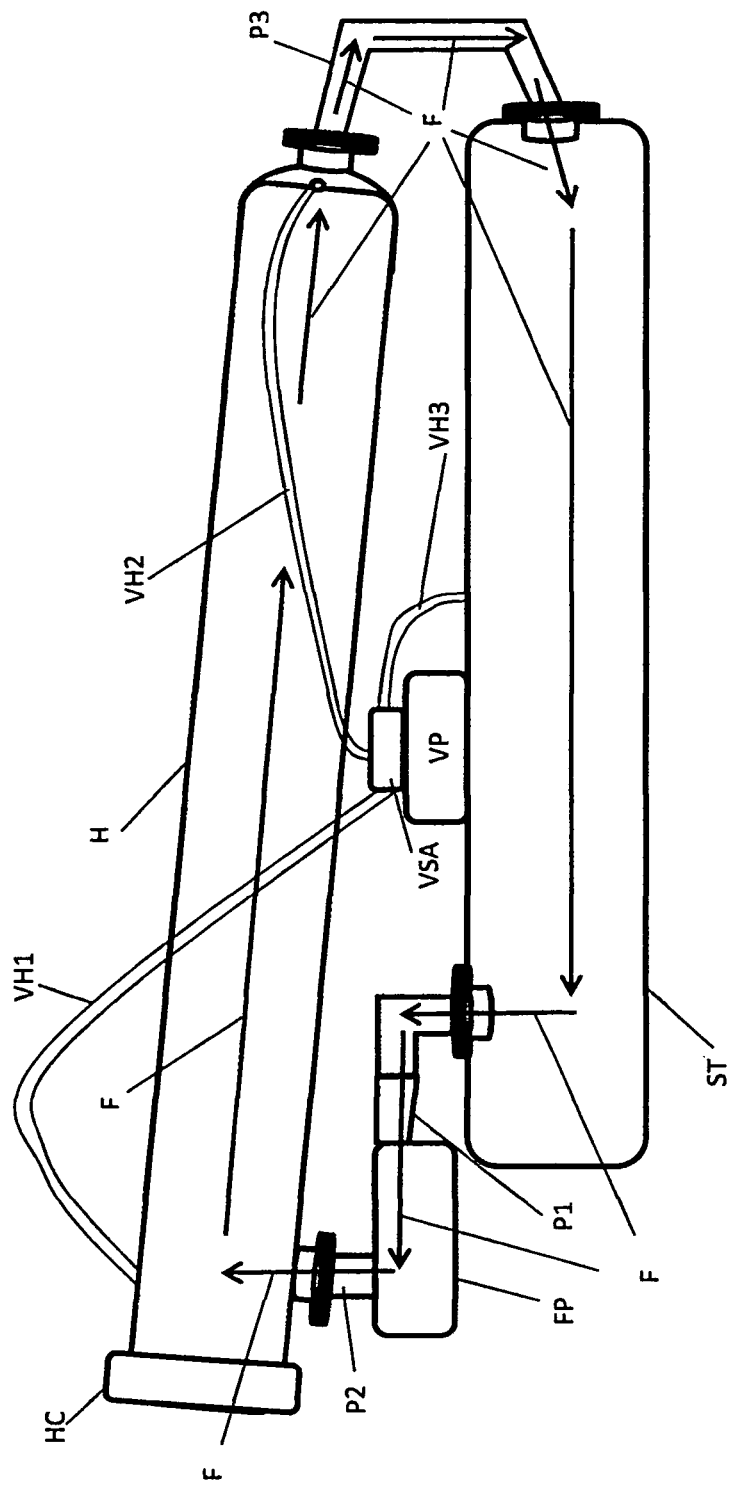
Figure 4: High Flow

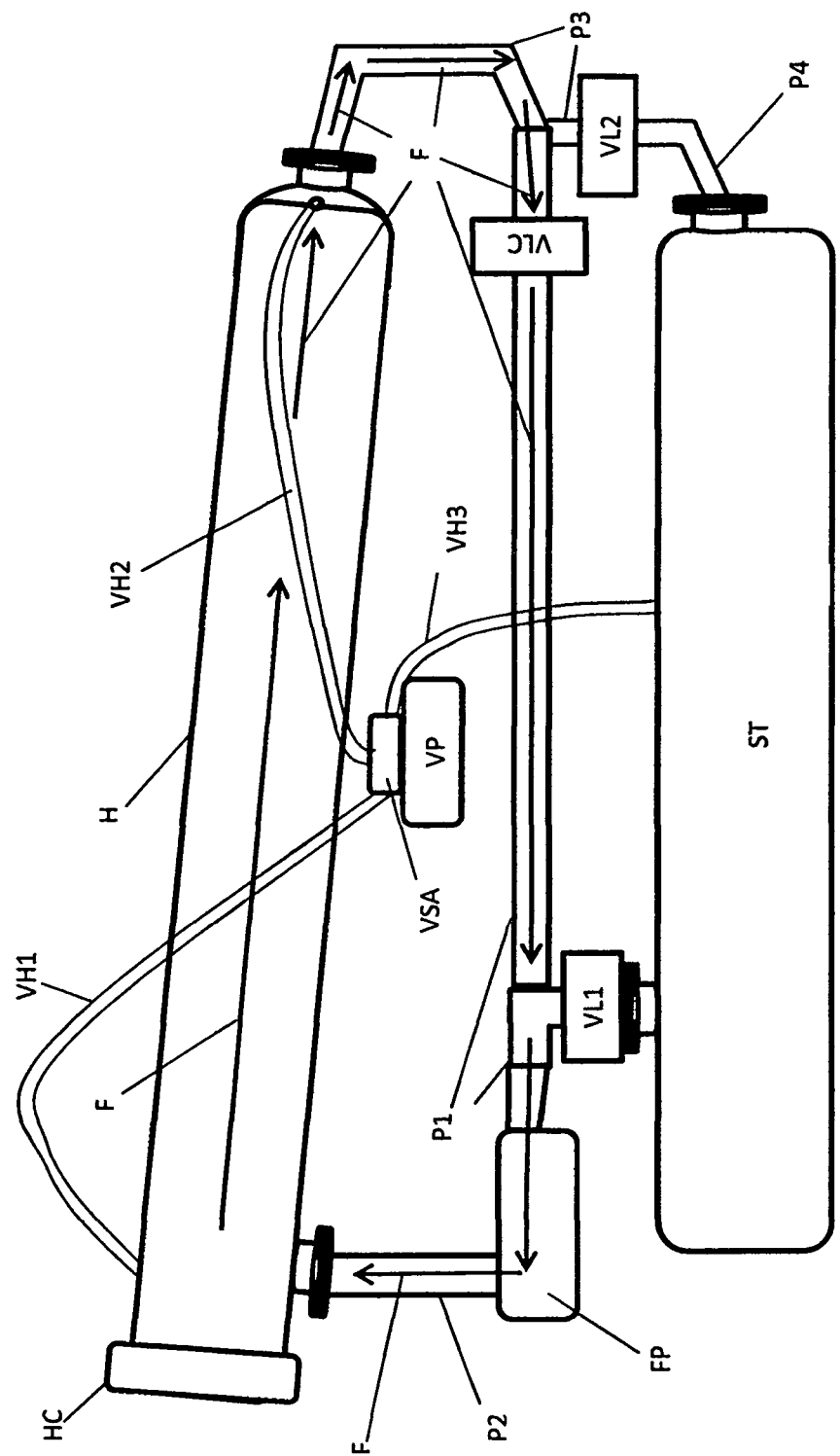
Figure 5: Low Volume High Flow

RECYCLING CANNABINOID EXTRACTOR

FEDERAL RESEARCH STATEMENT

Not Applicable

JOINT RESEARCH AGREEMENT

Not Applicable

SEQUENCE LISTING

Not Applicable

CROSS SECTION TO RELATED APPLICATIONS

None

BACKGROUND OF THE INVENTION

In past years various mechanisms for extracting essential elements from raw plant material have been researched by professional scientists, until recently the extraction of medicinal compounds from *cannabis* has been limited to small scale extractions by authorized scientists in the academic realm or has been performed clandestinely by individuals operating outside the law.

With the advent of legalizing the medicinal use of *cannabis* in 16 states the extraction of medicinal compounds from *cannabis* plant material in large volumes is in demand. The most significant driver for this demand are the increasing bodies of research showing tangible benefits to individuals suffering from a plurality of ailments when using medicinal *cannabis*. Furthermore no toxic or overdose effects from the use of *cannabis* have been medically documented.

*Cannabis* plant material contains tetrahydrocannabinol carboxylic acid (THC—COOH); this substance is also referred to as THC acid, Δ9-THC acid, THCA-A, or THCA.

The Journal of Chromatography article "Innovative development and validation of an HPLC/DAD method for the qualitative determination of major cannabinoids in *cannabis* plant material" reference [1], see section 1.1; reports that THC-B is another form of THC acid that appears only in trace amounts in *cannabis* plant material. This article also reports other substances in *cannabis* plant material, including cannabidiolic acid (CBDA) and cannabigerolic acid (CBGA); a substance cannabinol (CBN) is also reported present in aged *cannabis*.

THC acid may be converted into the psychoactive substance Tetrahydrocannabinol (THC), also known as ($\Delta^9$-THC) through processes that decarboxylates the THC acid. Decarboxylation is a chemical reaction that converts an acid to a phenol and releases carbon-dioxide (CO2) as a carbon atom is removed from a carbon chain.

Reference [1] also discusses and shows the decarboxylation of THC acid into $\Delta^9$-THC, the decarboxylation of cannabidiolic acid (CBDA) into cannibidiol (CBD), and the decarboxylation of cannabigerolic acid (CBGA) into cannabigerol (CBG). Decarboxylation occurs when *cannabis* is exposed to heat, light, cofactors or solvents.

Historical and anecdotal reports of the medicinal use of *cannabis* date back for millennia, in recent decades the psychoactive ingredient A9-THC has been extracted through a verity of processes; to date processes that decarboxylate of THCA-A into psychoactive $\Delta^9$-THC in controlled ways use toxic solvents; frequently a distillation process such as fractal distillation is then used to separate the toxic solvents from the active ingredient after decarboxylation. THCA-A decarboxylated into $\Delta^9$-THC in controlled ways using toxic solvents:

Related U.S. Pat. Nos. 6,365,416 B1 [2], 6,730,519 [3]; and patent publication US 2002/0039795 A1 [4] by Elsohly et. al. isolates $\Delta^9$-THC from *cannabis* base material using toxic non-polar organic solvents such as hexane, heptane, or iso-octane. U.S. Pat. No. 6,730,519 [3] was sponsored by a National Institute for Drug Abuse, Small Business Innovative Research grant; Related US Patent disclosures U.S. Pat. Nos. 6,365,416 [2] and 6,730,519 [3] in their Background of the Invention section provide excellent details regarding the medical use of $\Delta^9$-THC. the inventors conclude that extracting $\Delta^9$-THC from *cannabis* plant material is more cost effective than synthetically created FDA approved medicinal THC, and they reference prior art dating from 1942 through 1972 that relate to THC extraction or analysis of hashish and "red oil"; the processes referenced frequently use toxic elements such as carbon tetrachloride, benzene, N-dimethyl formamide/cyclohexane, or hexane.

U.S. Pat. Nos. 7,524,881 B2 [5], and 7,592,468 B2 [6] Goodwin et. Al. discloses processes that extract $\Delta^9$-THC from *cannabis* plant material; this process converts THC acid into salt using non-polar solvents such as pentane, hexane, heptane, or octane; again toxic or flammable solvents are used.

U.S. Pat. No. 7,344,736 B2 [7] and US Patent Application Publication US 2008/0167483 A1 [8] by Whittle et al (assignee GW Pharmaceuticals) entitled "Extraction of Pharmaceutically Active Materials From Plant Material" describe the use of liquid $CO_2$ to extract cannabinoids including THC and CBD from *cannabis* plant material.

U.S. Pat. No. 7,622,140 B2 [9] and US Patent Application Publication 2010/0119606 A1 [10] by Whittle et at (assignee GW Pharmaceuticals) entitled "Process and Apparatus for Extraction of Active Substances and Enriched Extracts from Natural Products" describes the use of high temperature gas to extract cannabinoids including THC and CBD from *cannabis* plant material. US Patent Application Publication US 2003/0017216 A1 [11] by Schmidt et al entitled "Isolation of Herbal and Cannabinoid Medicinal Extracts" describes that solvent extractions of *cannabis* for durations less than 5 minutes yield extracts of higher quality as they contain fewer non-therapeutic materials than extracts of a longer duration.

Throughout the balance of this disclosure the term medicinal *cannabis* compounds refers to cannabinoids in their decarboxylated state, in the acidic state, or in combination thereof. For example medicinal *cannabis* compounds include yet are not limited to $\Delta^9$-THC which is decarboxylated THC acid.

*Cannabis* is a high priced commodity, high quality *cannabis* wholesales today for around $3000 per pound and retails for around $6000 per pound ($375 per ounce). Because of this high valuation an extraction derived from a large amount of *cannabis* in concentrate is a target for theft and abuse.

California collectives and cooperatives are authorized to grow *cannabis* by state law for medicinal use. They are located throughout the state and are often separated by dozens or even hundreds of miles. The main products they provide for medicinal use are *cannabis* flowers commonly called buds. These flowers contain the greatest concentration of medicinal compounds, some varieties of *cannabis* buds contain 20% to 25% or more medicinal *cannabis* compounds by volume.

*Cannabis* plants also contain leaf and stems that are not typically utilized as medicinal *cannabis*, yet are typically used as mulch or fertilizer for growing other *cannabis* plants. This is because there is little to no market for leaf or stems because medicinal *cannabis* patients do not prefer leaf or stems. Leaf matter contains about 8% to 10% medicinal *cannabis* compounds by volume. Utilizing this as mulch wastes the medicinal *cannabis* contained within. California law also stipulates that *cannabis* be controlled and not used for non-medical use. Utilizing leaf matter as mulch may be considered by some as a non-medicinal use of *cannabis,* and may be in violation of California law. Another concern for lawmakers is the diversion of *cannabis* grown legally into illegal or illicit markets.

Extracting medicinal *cannabis* compounds from *cannabis* leaf matter eliminates waste and enables growers to control *cannabis* in accordance with State laws. The invention described within this disclosure is an apparatus and process that extracts medicinal compounds from *cannabis* plant material in large volumes, yet stores the extraction in a large volume of solvent. The invention eliminates waste and prevents diversion of *cannabis* into illegal or illicit markets by neutralizing cannabinoids within plant material.

BRIEF SUMMARY OF THE INVENTION

The invention described within this disclosure is an apparatus and process that extracts medicinal compounds from *cannabis* plant material in large volumes. It stores the extraction in low concentrations of medicinal *cannabis* compounds per unit volume of solvent and does so until the extraction can be moved to a secure location where it can be processed further.

Patent application Ser. No. 13/066,585 entitled Essential Element Extractor is hereby incorporated by reference into this patent application.

The invention includes a solvent tank, a hopper, and one or more pumps. The solvent tank is typically filled with a clean solvent that is free of contaminants. The hopper is a container where a large volume of *cannabis* plant material are introduced and then soaked, rinsed, and or washed with solvent from the solvent tank. Solvent from the hopper will be returned to the solvent tank at appropriate times. Solvent may also be circulated through the *cannabis* plant matter or solvent and *cannabis* plant matter may be circulated through the extraction apparatus or portion of the extraction apparatus enriching the solvent with cannabinoids. After an extraction is complete the *cannabis* plant matter is typically dried before it is removed from the system, and the cannabinoid enriched solvent is drained or transferred into the solvent tank.

Soaking, washing, and or rinsing *cannabis* plant material in solvent extracts or strips medicinal *cannabis* compounds from the plant matter and distributes it into the solvent forming a elution of medicinal *cannabis* compounds and solvent. Washing consists of the combined actions of soaking and rinsing, or may include additional steps like agitation (mechanical/acoustic), crushing, or mashing. Acoustic washing includes applying sonic or ultrasonic frequencies to solvent saturated *cannabis* in the apparatus typically using one or more sonic or ultrasonic transducers. Washing also includes the action of pumping a mixture of *cannabis* plant matter and solvent through the apparatus.

After the extraction process is complete the *cannabis* plant material contains little or no medicinal compounds as the solvent has extracted or stripped the medicinal compounds from the *cannabis* plant material. The extracted *cannabis* plant material may then be used as mulch without wasting medicinal cannabinoids. Processing *cannabis* in this manner prevents cannabinoids in from being diverted into elicit or illegal markets and can keep cannabinoids within a legal system.

After each extraction the hopper may be refilled with a new batch of *cannabis* plant material. At this point in time solvent in the solvent tank can be used again to extract cannabinoids from the latest batch of *cannabis* plant material. In this manner the extraction process may be performed many times increasing the concentration of cannabinoids in the solvent tank with each extraction by recirculating the solvent.

Even after extracting numerous hoppers of new *cannabis* plant material the *cannabis* enriched solvent solution will have a low concentration of medicinal *cannabis* compounds per unit volume of solvent making it an unattractive item to be stolen because a thief would have little or no facility for separating the medicinal *cannabis* compounds from the solvent.

The storing and moving of medicinal *cannabis* compounds in a dilute solvent solution is therefore a more secure way of transporting valuable medicinal *cannabis* compounds to a processing facility where the solvent and medicinal *cannabis* compounds may be separated. Another aspect or refinement of the invention is that medicinal cannabinoids may be transported in concentrations below Federal exemption levels.

Cannabinoids may then be separated from the solvent using additional process steps recovering clean solvent. The solvent is thus recycled back to a clean state and ready to be re-used. The process is considered green because the solvent is recycled mitigating solvent loss to the atmosphere. The apparatus facilitates extraction efficiency in a simple unit. The process provides in part transportation of cannabinoids in a diluted from where it cannot be readily utilized if stolen. Using a food grade solvent in the process insures that extracts containing medicinal *cannabis* are food grade, making them available for incorporation into consumable products containing medicinal *cannabis*.

DETAILED DESCRIPTION OF THE INVENTION

The invention described within this disclosure is an apparatus and process that extracts medicinal compounds from *cannabis* plant material in large volumes. It stores the extraction in low concentrations of medicinal *cannabis* compounds per unit volume of solvent and does so until the extraction can be moved to a secure location where it can be processed further.

Patent application Ser. No. 13/066,585 entitled Essential Element Extractor is hereby incorporated by reference into this patent application.

In certain embodiments the invention includes a solvent tank, a hopper, and one or more pumps. In other embodiments the invention also includes a filter vessel, pipes, valves, sensors, solenoids, and/or an electronic control system. Before any *cannabis* is processed the solvent tank is typically filled with a clean solvent.

The hopper is a container where a large volume of *cannabis* plant material are introduced prior to extraction, this *cannabis* plant matter is then soaked, rinsed, and or washed with solvent from the solvent tank.

In some embodiments of the invention the *cannabis* plant matter remains in the hopper during the extraction process. In these embodiments the *cannabis* plant matter will be retained in the hopper using one or more fitters, screens, filter bags, filter baskets, or other fine obstructions.

In other embodiments of the invention *cannabis* plant matter is circulated with solvent through at least a portion of the extraction apparatus and through the solvent pump. In these embodiments *cannabis* plant matter may be placed inside the hopper without a bag or filter typically after it has been chopped up, cut up, or broken up. In these embodiments the

*cannabis* raw material will typically be separated from cannabinoid enriched solvent after it has circulated for a time.

In this disclosure the term solvent pump refers to pumps that facilitate moving liquid solvent directly by pumping solvent through the pump. Solvent pumps include fuel pumps, gasoline pump, or any pump capable of pumping volatile liquids.

Vacuum pumps are pumps optimized for pumping gasses. Gasses include yet are not limited to air, solvent vapor, carbon dioxide, water vapor, and oxygen. Vacuum pumps have a vacuum input and a vacuum output. Because the vacuum input is where gas is sucked into the vacuum pump, and the vacuum output is where gas is exhausted the vacuum input is at a low pressure relative to the vacuum output.

In some embodiments of the invention vacuum is used to suck liquid solvent from one vessel to another without liquid necessarily passing through the vacuum pump. Just like sucking milk out of a glass through a straw, the straw can be filled without sucking milk into your mouth. In other embodiments the hopper and other parts of the system including pipes are filled with solvent from the solvent tank using vacuum. The term pipe or pipes in this disclosure refers to hard pipe, flexible pipe, hoses, couplings, tubes, or other connections capable of transferring liquids or gases from one place to another. The hopper input or output for example may itself be a pipe even if it is a rubber hose.

In one embodiment, the *cannabis* plant material is soaked for a time in the solvent, and then the solvent from the hopper is transferred back into the solvent tank. Then the wet *cannabis* plant material may be then rinsed with solvent by transferring more solvent from the solvent tank through the wet *cannabis* plant material and back into the solvent tank using one or more pumps.

In another embodiment, the *cannabis* plant material is rinsed with solvent by transferring solvent from the solvent tank through the *cannabis* plant matter and into the solvent tank without soaking the *cannabis* plant material in solvent for a time.

Soaking, washing, and or rinsing *cannabis* plant material in solvent chemically extracts or strips medicinal *cannabis* compounds from the plant matter and distributes it into the solvent forming an elution of medicinal *cannabis* compounds and solvent. Washing consists of the combined actions of soaking and rinsing, or may include additional steps like agitation (mechanical/acoustic), crushing, or mashing. Acoustic washing includes applying sonic or ultrasonic frequencies to solvent saturated *cannabis* in the apparatus typically using one or more sonic or ultrasonic transducers. Washing also includes the action of pumping a mixture of *cannabis* plant matter and solvent through the apparatus.

A vacuum pump, a solvent pump, and or gravity feed or combination thereof may be used to transfer the solution of medicinal *cannabis* compounds and solvent from the hopper or a filter vessel to the solvent tank.

Some embodiments of the invention utilize a vacuum pump to transfer the solution of medicinal *cannabis* compounds between the hopper or a filter vessel and the solvent tank.

Most vacuum pumps are not designed to pump liquids directly yet are capable of passing solvent vapor and small quantities of liquid solvent without damaging the vacuum pump. Because of this vacuum pumps may be used to dry wet or damp *cannabis* after cannabinoids have been extracted from the *cannabis*. Drying solvent wetted *cannabis* plant material prevents solvent from being lost in the atmosphere through evaporation. Various configurations for vacuum drying may be incorporated into the invention.

One drying configuration is where vacuum pressure is applied to the top of the hopper or filter vessel and vacuum is applied to the bottom of the hopper or filter vessel. In this instance the vacuum pump establishes a flow of gas through the *cannabis* plant material drying it. Solvent vapor condenses and then drains out of the hopper or filter vessel.

Another drying configuration is where valves connecting to the hopper or filter vessel are closed, a vacuum is applied to the hopper or filter vessel, and the vacuum pressure output of the vacuum pump is output into the solvent tank. This configuration causes solvent to evaporate from the *cannabis* plant matter as pressure in the hopper or filter vessel reduces. Solvent vapor is then passed through the vacuum pump and into the solvent tank where it condenses into a liquid.

Still other embodiments of the invention use solvent pumps to transfer solvent between the solvent tank and the hopper or filter vessel when draining the hopper, when rinsing, or when filtering. Solvent pumps may also pump or push solvent back into the solvent tank when filling or rinsing. Some configurations use one solvent pump to fill the hopper and a second solvent pump to empty it. In these embodiments vacuum pumps may or may not be used. The invention does not require the use of vacuum.

In yet other embodiments the hopper and/or the solvent tank are vessels built to withstand pressure and/or vacuum.

After the extraction process is complete spent *cannabis* plant matter is emptied from the hopper. At this point the *cannabis* plant matter contains little or no medicinal compounds as the solvent has extracted or stripped the medicinal compounds from the *cannabis* plant matter.

Embodiments of the invention that keep the *cannabis* plant matter in the hopper are emptied by opening the hopper and removing or dumping the *cannabis* plant matter.

Embodiments of the invention that circulate a *cannabis* plant matter and solvent through the system or portion of the system include a step for separating the *cannabis* plant matter from cannabinoid enriched solvent.

After the extraction process the *cannabis* plant matter contains few or no cannabinoids. The *cannabis* plant matter may then be used as mulch without wasting medicinal cannabinoids. Processing *cannabis* in this manner prevents cannabinoids in from being diverted into elicit or illegal markets. This means that farmers or producers of legal medicinal *cannabis* can keep all of their cannabinoids within the medicinal *cannabis* legal system because cannabinoids even in waste *cannabis* may be processed and used in legal medicinal *cannabis* products. After each extraction the hopper may be refilled with a new batch of *cannabis* plant matter. At this point in time solvent in the solvent tank can be used again to extract cannabinoids from the latest batch of *cannabis* plant material. In this manner the extraction process may be performed many times increasing the concentration of cannabinoids in the solvent tank with each extraction by recirculating the solvent.

Even after extracting numerous hoppers of new *cannabis* plant material the *cannabis* enriched solvent solution will have a low concentration of medicinal *cannabis* compounds per unit volume of solvent making it an unattractive item to be stolen because a thief would have little or no facility for separating the medicinal *cannabis* compounds from the solvent.

The storing and moving of medicinal *cannabis* compounds in a dilute solvent solution is therefore a more secure way of transporting valuable medicinal *cannabis* compounds to a processing facility where the solvent and medicinal *cannabis* compounds may be separated. Another aspect or refinement of the invention is that medicinal cannabinoids may be transported in concentrations below Federal exemption levels. Cannabinoid concentrations of 1 milligram per milliliter and below are not and not considered to be a drug by Federal laws.

Cannabinoids may then be separated from the solvent using additional process steps recovering clean solvent. The solvent is thus recycled back to a clean state and ready to be re-used. The process is considered green because the solvent is recycled mitigating solvent loss to the atmosphere. The apparatus facilitates extraction efficiency in a simple unit. The process provides in part transportation of cannabinoids in a diluted from where it cannot be readily utilized if stolen. Using a food grade solvent in the process insures that extracts containing medicinal *cannabis* are food grade, making them available for incorporation into consumable products containing medicinal *cannabis*.

Embodiments of the invention that utilize a vacuum pump to transfer the solution of medicinal *cannabis* compounds between two vessels, i.e. between the hopper and the solvent tank, or between the solvent tank and the hopper typically do so by drawing a vacuum on the destination vessel above the level of the liquid in the destination vessel. A tube, pipe, or hose connecting the two vessels together that extends below the liquid level in the source vessel will typically be used to draw liquid from the source vessel to the destination vessel. In such a configuration the low pressure in the destination vessel will cause liquid to be sucked from the source vessel to the destination vessel without sucking the liquid through the vacuum pump.

Embodiments of the invention where *cannabis* plant matter remains in the hopper can simply be emptied from the hopper by dumping the hopper, or by grabbing and lifting a filter bag or basket out of the hopper.

Embodiments of the invention where *cannabis* plant matter is circulated to some or all of the apparatus include a filtering step. In some of these embodiments the circulating slurry of *cannabis* plant matter and solvent are directed into a filter or screen after the extraction is complete; in these embodiments the filter may be in a separate filter vessel be attached to the hopper, or be inserted into the hopper at a certain point in the process.

Instances when a separate filter vessel is used to separate the *cannabis* plant matter from the cannabinoid enriched solvent using one or more filters, screens, filter bags, filter baskets, or other fine obstructions in or connected to the filter vessel.

In these embodiments the slurry of *cannabis* plant matter and solvent are circulated through at least the hopper, a solvent pump, and interconnecting pipes. When the extraction is complete a valve directs the slurry into the separate filter vessel where the *cannabis* plant matter is captured in the filter vessel while the cannabinoid enriched solvent flows into the solvent tank.

In instances where the circulating slurry of *cannabis* plant matter are filtered out using the hopper the *cannabis* plant matter may be trapped in the hopper in various ways. Here again one or more filters, screens, filter bags, filter baskets, or other fine obstructions separate *cannabis* plant matter from cannabinoid enriched solvent.

One such embodiment uses multi position valve on the bottom of the hopper. In one orientation the multi position valve would allow unrestricted flow, in another orientation the valve would contains a filter or screen that is used to trap the *cannabis* plant matter.
Another such embodiment, the circulation system is turned off and the hopper is drained. Screens would also typically be used to prevent *cannabis* plant matter from flowing into the solvent tank when the hopper is drained.

After the hopper is drained of solvent, a filter is inserted into the hopper by an operator, the hopper is sealed, and the system is restarted. Restarting the circulation with a filter added in the hopper captures the *cannabis* plant matter in the hopper. At this time the cannabinoid enriched solvent would be directed into the solvent tank.

The density of cannabinoids in the solvent tank will depend on several factors that include: the total volume of solvent in the solvent tank; the dry weight of *cannabis* plant material extracted; the average amount of cannabinoids in the *cannabis* plant material; and the average extraction efficiency of the process. Estimates of these factors may be made at the time an extraction is performed; the process may be managed based on the estimated amount of *cannabis* processed into a volume of solvent such that a target estimated cannabinoid concentration would be mixed into the solvent per unit volume of the solvent. Cannabinoid concentrations of 1 milligram per milliliter and less are not considered drugs by Federal standards and statutes.

The storing and moving of medicinal *cannabis* compounds in a solvent solution is a secure way of transporting valuable medicinal *cannabis* compounds as thieves would not have the facility for removing the *cannabis* from the solvent even if they knew what it was.

Preferred solvents include yet are not limited to a non-polar food grade solvent such as hexane and heptane:

A preferred embodiment of the invention is built onto a light truck or some form of vehicle; a vehicle in this disclosure includes a trailer; the invention is not limited to being mounted on a vehicle yet may be built using multiple vehicles.

In one embodiment one or more solvent pumps are used to rinse *cannabis* plant material in the hopper by moving solvent from the solvent tank, to the hopper, and then back to the solvent tank continuously. In this embodiment solvent will typically be pumped into an input of the hopper and returned to the solvent tank through an output of the hopper. After the *cannabis* has been rinsed for a time the hopper is drained. In one embodiment at this point vacuum pumps pressurize the top of the hopper and provide a vacuum to the bottom of the hopper through the source tank. Valves, solenoids, or a solvent pump in line with the may also be used to close the solvent input line connected on or near the top of the hopper. The vacuum pump will provide a flow of air or gas through the *cannabis* drying it. Such and embodiment may include one or more liquid traps such as a Woulff bottle.

In another embodiment of the invention the hopper is filled using solvent pumps, vacuum pumps, or combination thereof and the *cannabis* is soaked for a time. In some embodiments if vacuum is used when filling the hopper, the pressure output of a vacuum pump will pressurize the solvent tank and the vacuum port of the vacuum pump will be applied to the hopper. Typically at this time any flow from the bottom of the hopper will be blocked either by a valve, solenoid valve, a fuel pump, or other obstruction.

In some embodiments when vacuum is used during draining, the pressure output from a vacuum pump may be applied to the hopper and the vacuum port for that vacuum pump may be applied to the solvent tank. Embodiments of the invention may also include one or more or combination of valves, solenoid valves, fuel/solvent pumps.

Embodiments of the invention that do use vacuum for some process steps may also use a rinse cycle where solvent pumps facilitate rinsing.

In some embodiments of the invention the hopper is filled with *cannabis* plant material, sealed, and then filled with solvent from the solvent tank. A solvent pump then begins circulating of solvent and *cannabis* plant material through the hopper, through pipes, and back through the solvent pump again and again. In some such embodiments the solvent tank is switched out of the switched out of the circuit with a valve; at the end of the extraction the slurry of solvent and *cannabis* plant matter is directed into a filter vessel where extracted *cannabis* plant matter is separated from the cannabinoid enriched solvent. In this instance typically the plant matter will then be captured by a filter or screen and the cannabinoid enriched solvent will be transferred to the solvent tank. Some such embodiments of the invention the system include a solvent tank, a solvent pump, pipes, valves, a hopper, and a filter vessel. In yet other embodiments of the invention the hopper also serves to separate *cannabis* plant matter from cannabinoid enriched solvent. Preferred pumps for embodiments of the invention that circulate a solvent and *cannabis* plant matter slurry through the pump are pumps made by Discflo Corporation. The invention is not limited to using pumps made by Discflo Corporation.

A first series of process steps for using some embodiments of the invention when *cannabis* plant material is contained within the hopper:
  a. The hopper is filled with *cannabis* plant material, typically by an operator.
  b. The hopper is then sealed before transferring solvent to the hopper.
  c. Solvent is transferred into the hopper.
  d. Solvent is circulated through at least the hopper and through at least one solvent pump.
  e. Solvent circulation is stopped and the solvent enriched with cannabinoids is drained or transferred to the solvent tank.
  f. Wetted *cannabis* plant matter is dried.
  g. The apparatus is put into an idle state.
  h. *cannabis* plant matter is removed from the apparatus.
  i. The process is then repeated.

A second series of process steps for using some embodiments of the invention when *cannabis* plant material is contained within the hopper:
  a. The hopper is filled with *cannabis* plant material, typically by an operator.
  b. The hopper is then sealed before transferring solvent to the hopper.
  c. Solvent is transferred into the hopper.
  d. A sonic or ultrasonic transducer connected to the hopper is activated.
  e. Solvent is circulated through at least the hopper and through at least one solvent pump.
  f. Solvent circulation and the sonic or ultrasonic transducer are stopped and the solvent enriched with cannabinoids is drained or transferred to the solvent tank.
  g. Wetted *cannabis* plant matter is dried.
  h. The apparatus is put into an idle state.
  i. *cannabis* plant matter is removed from the apparatus.
  j. The process is then repeated.
  An operator an electronic control system or combination thereof may perform one or more of these process steps.

A first series of process steps for using some embodiments of the invention when *cannabis* plant material and solvent are circulated through at least a portion of the apparatus:
  a. The hopper is filled with *cannabis* plant material, typically by an operator.
  b. The hopper is then sealed before transferring solvent to the hopper.
  c. Solvent is transferred into the hopper.
  d. A sonic or ultrasonic transducer in fluid communication with the solvent is activated.
  e. Solvent and *cannabis* plant matter are circulated through at least the hopper and through at least one solvent pump.
  f. Solvent and *cannabis* plant matter are directed into a filter vessel where *cannabis* plant matter is separated from cannabinoid enriched solvent.
  g. Solvent circulation and the sonic or ultrasonic transducer are stopped and the solvent enriched with cannabinoids is drained or transferred to the solvent tank.
  h. Wetted *cannabis* plant matter is dried.
  i. *cannabis* plant matter is removed from the apparatus.
  j. The process is then repeated.
  An operator an electronic control system or combination thereof may perform one or more of these process steps. Additional process steps may be included including yet not limited to introducing filter bags, or filter baskets into the hopper or filter vessel.

A second series of process steps for using some embodiments of the invention when *cannabis* plant material and solvent are circulated through at least a portion of the apparatus::
  a. The hopper is filled with *cannabis* plant material, typically by an operator.
  b. The hopper is then sealed before transferring solvent to the hopper.
  c. Solvent is transferred into the hopper.
  d. Solvent and *cannabis* plant matter are circulated through at least the hopper and through at least one solvent pump.
  e. Solvent and *cannabis* plant matter are directed into a filter or screen on the bottom of hopper where *cannabis* plant matter is separated from cannabinoid enriched solvent.
  f. Solvent circulation is stopped and the solvent enriched with cannabinoids is drained or transferred to the solvent tank.
  g. Wetted *cannabis* plant matter is dried.
  h. *cannabis* plant matter is removed from the apparatus.
  i. The process is then repeated.
  An operator an electronic control system or combination thereof may perform one or more of these process steps. Additional process steps may be included including yet not limited to introducing filter bags, or filter baskets into the fitter vessel.

A third series of process steps for using some embodiments of the invention when *cannabis* plant material and solvent are circulated through at least a portion of the apparatus:
  a. The hopper is filled with *cannabis* plant material, typically by an operator.
  b. The hopper is then sealed before transferring solvent to the hopper.
  c. Solvent is transferred into the hopper.
  d. Solvent and *cannabis* plant matter are circulated through at least the hopper and through at least one solvent pump.
  e. The circulation is stopped and the hopper is drained.
  f. A filter bag, screen, or basket is inserted into the hopper.
  g. Solvent is transferred into the hopper.
  h. Solvent and *cannabis* plant matter are pumped through the hopper with a solvent pump separating *cannabis* plant matter from the cannabinoid enriched solvent.

i. Solvent circulation is stopped and the solvent enriched with cannabinoids is drained or transferred to the solvent tank.
j. Wetted *cannabis* plant matter is dried.
k. *cannabis* plant matter is removed from the apparatus.
l. The process is then repeated.

An operator an electronic control system or combination thereof may perform one or more of these process steps. Additional process steps may be included including yet not limited to introducing filter bags, or filter baskets into the filter vessel.

The solvent may be introduced into the hopper by using one or more vacuum pumps, solvent pumps, gravity feed, or combination thereof. The hopper or a filter vessel may be drained using one or more vacuum pumps, solvent pumps, gravity feed, or combination thereof Applicant notes that the embodiments listed above are examples of the invention, they are provided for illustrative purposes and are not intended to limit the invention. The invention is not limited to embodiments reviewed above. Applicant also notes that depending on a given embodiment of the invention vacuum pumps may or may not be used, that vacuum pumps may assist fuel/solvent pumps, and that fuel/solvent pumps may not be used when vacuum pumps are used. Minor variations or changes in topology are considered to be alternate embodiments of the invention. For example, the location of a vessel's liquid input or output ports may exit the vessel from the top, bottom, or side of the vessel and still be an embodiment of the invention.

A preferred mode of the invention also includes an electronic control system that activates pumps and/or valves incorporated into an embodiment of the invention; the electronic control system implementing various sequences of the process including filling the hopper with solvent, draining solvent from the hopper, rinsing the *cannabis*, and/or drying the *cannabis*.

The electronic control system may also contain sensors measuring the solvent levels, the pressure, and/or the temperature in the hopper and the tanks; for example in some embodiments, if an excessive amount of solvent is contained within the hopper or in a tank the system will react appropriately to prevent overfilling, spilling, or over pressurization of the solvent. Ideally the electronic control system will include a micro-computer that is programmed to perform orderly extractions and react appropriately to fault conditions.

The use of vacuum at least during at least some of the process steps (especially drying) is preferred because hexane, heptane, and other solvents are flammable; the vacuum lowers the pressure, removes oxygen, and reduces the likelihood of the hexane vapors combusting. The perfect gas law state that Pressure (P) times Volume (V) equals the number of moles (n) of the gas times a constant R time Temperature: $PV=nRT$. When the pressure is lowered by the vacuum the temperature of the hexane gas vapors will reduce significantly and oxygen will be purged from the system or reduced in the system. Lower temperatures and lack of oxygen decreases the likelihood of combustion significantly.

Contents of the solvent tank may be processed further at a distant location typically by using a rotary evaporator such as a Bucci Rotavapor Model 124 or a wiped film evaporator. These types of evaporators are commonly used in the food service and pharmaceutical industries to separate elements from a solvent. Since the vapor pressure of a solvent is much lower than the essential elements, the solvent is evaporated then condensed in a clean chamber leaving a concentrated extract behind. Clean and pure condensed solvent will be separated from a concentrate of essential elements from the plant material. At this point clean solvent will be added back into the solvent tank of the extractor and a concentrate of essential elements from the plant material are available for incorporation into medicinal products.

Cannabinoids may thus be separated from the solvent using additional process steps recovering clean solvent. The solvent is thus recycled back to a clean state and ready to be re-used. The process is considered green because the solvent is recycled mitigating solvent loss to the atmosphere. The apparatus facilitates extraction efficiency in a simple unit. The process provides in part transportation of cannabinoids in a diluted from where it cannot be readily utilized if stolen. Using a food grade solvent in the process insures that extracts containing medicinal *cannabis* are food grade, making them available for incorporation into consumable products containing medicinal *cannabis*.

FIG. 1 entitled "Mobile Extractor in Semi Cross Section" shows:

A solvent tank ST filled with a portion of solvent S; a hopper H with hopper cover HC is connected to the solvent tank ST by a hose or pipe HS, portions of the hose or pipe HS within the source tank ST and within the hopper H are shown with dashed lines indicating that a portion of the hose or pipe HS is inside the hopper H and inside the solvent tank ST.

Inside of the hopper H is a nozzle N (shown with dashed lines) and plant material PM is shown in gray. The hopper is connected to a hopper valve HV that leads back to the solvent tank ST through pipe P. When the hopper valve is closed solvent will not flow from the hopper H to the solvent tank ST; in alternate embodiments HV can be or include a solvent pump. The hopper also is depicted as having a vent, item VN.

A solvent valve SV is located on the solvent tank and is attached to hose or pipe HS, the solvent valve when open in some embodiments will allow solvent S to be sucked into the hopper by the vacuum pump VP through hose or pipe HS. When closed solvent valve SV will block the flow of solvent CS from the solvent tank to the hopper. Item SV alternatively may be a conventional solvent pump used to pump solvent from the solvent tank to the hopper.

Vacuum hoses VH1 and VH2 are connected to a vacuum solenoid valve array VS. Vacuum hose VH1 is connected to the hopper H, and vacuum hose VH2 is connected to the solvent tank ST. The vacuum solenoid array VS is connected to the vacuum pump VP and is capable of applying vacuum to the hopper H or to the solvent tank ST. The vacuum solenoid array VS is also capable of applying vacuum pressure to the hopper or to the solvent tank ST.

When vacuum is applied to hopper, vacuum pressure is applied to the solvent tank ST, and when solvent valve SV is open liquid solvent S will be sucked from the solvent tank ST into the hopper H soaking plant material PM and priming the system with liquid solvent.

In some embodiments solvent valve SV contains a solvent pump, in these embodiments solvent may be pumped into the hopper with or without the use of vacuum.

When hopper valve HV is open gravity will pull solvent S back into the solvent tank ST from the hopper H through pipe P.

Typically a screen or filter (not depicted) located between the hopper H and the hopper valve HV will prevent plant material PM from falling into the solvent tank ST. A portion of pipe P extending into the solvent tank ST is shown with dashed lines.

Vacuum may also be used to facilitate moving solvent S back into the solvent tank ST from the hopper H. In this instance vacuum pressure is typically applied to the hopper and vacuum is applied to the solvent tank. In yet other embodiments hopper valve HV also includes a solvent pump capable of transporting solvent S back into the solvent tank from the hopper H. The invention may use gravity, vacuum, and/or pumping when moving solvent.

Rinsing the plant material may be performed with or without vacuum:

In one embodiment when vacuum is not applied during rinse, when item SV is configured to be a solvent pump, liquid solvent will be pumped from the solvent tank into the hopper. Pressure from this pumping, gravity, a second solvent pump, or combination may be used to move solvent from the hopper to the solvent tank through item HV and pipe P. Item HV in some embodiments may be a solvent pump, in other embodiments it may be a valve.

In other embodiments rinse may be performed while both the hopper H and the solvent tank ST are both under vacuum.

Also connected to the clean tank is input valve IV, this valve is typically closed, yet may be opened to add more clean solvent into the solvent tank ST.

Another valve, the drain valve DV is connected to the bottom of the solvent tank ST, the drain valve DV is typically closed, yet when open will cause the solvent S to drain out of the solvent tank ST.

FIG. 2: entitled "A Mobile Extractor Mounted on a Truck" shows:

FIG. 2 shows many of the same elements as FIG. 1 yet in FIG. 2 the apparatus is mounted on a truck T. The hopper H, hopper cover HC, vent VN, hopper valve or solvent pump HV, pipe P, solvent valve or solvent pump SV, hose or pipe HS, solvent tank ST, and input valve IV depicted in FIG. 2 are capable of performing all of the same actions as the apparatus shown in FIG. 1.

Here again solvent valve or solvent pump SV is connected to the hopper H by a hose or pipe HS; the hopper H is connected to a hopper valve or solvent pump HV which in turn is connected to pipe P, and pipe P is connected to solvent tank ST. For sake of clarity the vacuum pump, vacuum hoses, vacuum valves, and the drain valve that were depicted in FIG. 1 are not shown in FIG. 2.

FIG. 3: entitled "Hopper Configured for Dumping" depicts a wheel barrow shaped hopper H on truck T.

The top figure in FIG. 3 shows the hopper H in its working position. Also depicted are hopper cover HC with a hinge HN, hose HS, solvent valve or solvent pump SV, the solvent tank ST a hopper valve or solvent pump HV, a pipe P connecting the hopper valve or solvent pump HV to the solvent tank ST, and input valve IV. Item R is a rotational member; it is an apparatus that allows the hopper H to be rotated and dumped.

The bottom figure in FIG. 3 shows all of the elements mentioned above (hopper H, hinge HN, hopper cover HC, hose HS, solvent valve or fuel pump SV, solvent tank ST, hopper valve or solvent pump item HV, pipe P, input valve IV, and rotational member R) yet shows the hopper H in the dumping configuration where hopper cover HC opens using hinge HN; this allows contents of the hopper H to be dumped. Also depicted is adaptor A, in this embodiment adaptor A allows the hopper to be connected to the hopper valve or solvent pump HV in a secure way.

Note that hose HS connects to the hopper near the point of rotation R of the hopper H; this allows the hopper H to be dumped without stressing or pulling on the hose HS.

FIG. 4 entitled "High Flow" depicts an embodiment of the invention where solvent is pumped at high velocities and possibly at higher than atmospheric pressure.

Item H is the hopper, item HC is a hopper cover, item ST is the solvent tank, item FP is a solvent pump; items P1, P2, and P3 are pipes. Pipes P1 connect the solvent tank ST to a solvent pump FP. Pipes P2 connect the solvent pump FP to the hopper H. Pipes P3 connect the hopper H to the solvent tank ST.

When rinsing, the solvent pump FP pumps solvent in a flow F from the solvent tank ST, through pipes P1, then through the solvent pump FP, through more pipes P2, then into the hopper H, and back into the solvent tank ST through more pipes P3. Arrows indicating solvent flow F through the apparatus during rinse are shown in FIG. 4.

A vacuum pump VP, a vacuum solenoid array VSA, and several vacuum hoses VH1, VH2, and VH3 are also depicted in FIG. 4.

The vacuum solenoid array VSA may be configured to provide vacuum or pressure inputs/outputs of the vacuum pump VP to the top of the hopper using vacuum hose 1 VH1, to the bottom of the hopper through vacuum hose 2 VH2, and/or to the solvent tank ST using vacuum hose 3 VH3.

In some embodiments the vacuum solenoid array VSA can provide vacuum or pressure to the solvent tank ST (through VH3), to the top of the hopper H (through VH1), and/or to the bottom of the hopper (through VH2).

Vacuum assisted priming the solvent pump FP may be performed by providing vacuum to the top of the hopper H through vacuum hose 1 VH1 near the output of the solvent pump FP, and by providing pressure the solvent tank ST through vacuum hose 3 VH3. Liquid solvent will tend to pushed up pipe P that feeds the solvent pump FP and vacuum applied near the top of the hopper H above the solvent pump FP will tend to suck solvent through the pump reducing the amount of work that the solvent pump FP pump needs to do to prime itself. Typically the vacuum pump VP will be turned off before the solvent pump FP is started.

Once the solvent pump FP is started solvent will flow F will recirculate through the system: from the solvent tank ST, through the pipe P feeding the solvent or fuel pump FP, through the pipe P feeding the hopper H, through the hopper H, exiting the hopper H through pipe P at the bottom of the hopper H, and back into the solvent tank ST. Solvent flow F through the system is depicted by arrows in FIG. 4.

After solvent has been recirculated for a desired amount of time the solvent pump FP will be turned off. Gravity will cause liquid solvent in the hopper H to drain into the solvent tank ST through pipes P1 and P3.

*Cannabis* plant material (not depicted in FIG. 4) inside of the hopper may be dried by turning on the vacuum pump VP, vacuum solenoid array VSA providing pressure to the top of the hopper H through vacuum hose 1 VH1 and providing vacuum at the bottom of the hopper H through vacuum hose 2 VH2 will cause air to circulate through the hopper drying the *cannabis* plant material. Alternatively vacuum may be applied to the solvent tank ST using vacuum hose 3 when pressure is applied to the top of the hopper H through vacuum hose 1 VH1 drying the *cannabis* plant material.

Once the *cannabis* plant material has been dried for a time the vacuum pump VP will be turned off and the hopper H will be emptied.

The high flow rate system depicted in FIG. 4 will preferably be built using pipes P, a hopper H, and a solvent tank ST that are capable of withstanding pressure and that will not collapse when exposed to vacuum.

FIG. 5 entitled Low Volume High Flow depicts another embodiment of the invention where solvent is pumped at high velocities and possibly at higher than atmospheric pressure through a small circulating system.

FIG. 5 contains all of the same items shown in FIG. 4. Item H is the hopper, item HC is a hopper cover, item ST is the solvent tank, item FP is a solvent pump, Pipes P1, P2, and P3, item VP is a vacuum pump, item VSA is a vacuum solenoid array, item VH1 is vacuum hose 1, item VH2 is vacuum hose 2, item VH3 is vacuum hose 3.

FIG. 5 also shows three valves VL1, VL2, and VLC; and Pipes P4.

Valve VL1 connects the solvent tank ST to the input of the solvent pump FP through pipes P1. Pipes P2 connect the output of the solvent pump FP to hopper H. Valve VL2 connects the bottom of the hopper H through pipes P3, and to the solvent tank ST through pipes P4. Valve VLC connects the bottom of the hopper through pipes P3 and P1 to the input of the solvent pump FP.

The embodiment of the invention depicted in FIG. 5 is capable of circulating solvent without circulating it through the solvent tank. Instead the solvent may be circulated using solvent pump FP through the hopper H and pipes P1, P2, P3, and back to the solvent pump FP.

Valves VL1, VL2, and VLC are used to switch the flow of liquid in the system. When valve VL1 is open solvent from the solvent tank ST may be introduced into the hopper H, pipes P1, P2, P3, and solvent pump FP in various ways. The system may be primed using a vacuum, vacuum assist, or using a solvent pump. During priming valve VL2 can be open or closed.

After the pipes P, hopper H, and solvent pumps are full or predominantly full of solvent valve VL1 will be closed, valve VLC will be open, and valve VL2 will be closed. At this point the solvent pump FP will be started. Solvent will then circulate through pipes P1, solvent pump FP, pipes P2, hopper H, pipes P3, valve VLC, and back to the solvent pump FP. Solvent flow F is depicted with arrows in FIG. 5. Some such embodiments of the can be configured to circulate a solvent and *cannabis* plant matter slurry.

A vacuum pump VP, a vacuum solenoid array VSA, and several vacuum hoses VH1, VH2, and VH3 are also depicted in FIG. 5.

The vacuum solenoid array VSA may be configured to provide vacuum or pressure inputs/outputs of the vacuum pump VP to the top of the hopper using vacuum hose 1 VH1, to the bottom of the hopper through vacuum hose 2 VH2, and/or to the solvent tank ST using vacuum hose 3 VH3. In some embodiments the vacuum solenoid array can provide vacuum or pressure to the solvent tank ST (through VH3), to the top of the hopper H (through VH1), and/or to the bottom of the hopper (through VH2).

Vacuum assisted priming the solvent pump FP may be performed by providing vacuum to the top of the hopper H through vacuum hose 1 VH1 near the output of the solvent pump FP, and by providing pressure the solvent tank ST through vacuum hose 3 VH3. Liquid solvent will tend to pushed up pipe P that feeds the solvent pump FP and vacuum applied near the output of the solvent pump FP will tend to suck solvent through the pump reducing the amount of work that the solvent pump FP pump needs to do to prime itself. Typically the vacuum pump VP will be turned off before the solvent pump FP is started.

After solvent has been recirculated for a desired amount of time valve VL1 will be opened and valve VLC will be closed, and solvent pump FP will be turned off. Gravity will cause liquid solvent in the hopper H to drain into the solvent tank ST through pipe P at the bottom of the hopper H.

If valves VL1 and VL2 were open, and valve was VLC closed when the solvent pump FP was running solvent would pumped from the solvent tank, through the hopper, and back into the solvent tank.

Here again *cannabis* plant material (not depicted in FIG. 5) inside of the hopper may be dried by turning on the vacuum pump VP, vacuum solenoid array VSA providing pressure to the top of the hopper H through vacuum hose 1 VH1 and providing vacuum at the bottom of the hopper H through vacuum hose 2 VH2 will cause air to circulate through the hopper drying the *cannabis* plant material. Alternatively vacuum may be applied to the hopper H using vacuum hose 1 VH3 when pressure is, applied to the top of the solvent tank ST through vacuum hose 3 VH3 drying the *cannabis* plant material.

Once the *cannabis* plant material has been dried for a time the vacuum pump VP will be turned off and the hopper H will be emptied.

Embodiments of the invention that circulate both *cannabis* plant matter and cannabinoid enriched solvent will typically have a way to filter the *cannabis* plant matter from the cannabinoid enriched solvent.

The invention is not limited to embodiments shown in the drawings or described above. For example the invention may include a filter vessel for separating *cannabis* plant matter from cannabinoid enriched solvent. In such an embodiment a series of valves would switch the *cannabis* solvent slurry into a filter vessel where *cannabis* plant matter would be entrapped and cannabinoid enriched solvent would typically be directed into the solvent tank.

Yet other embodiments of the invention include the instance where *cannabis* plant matter is introduced into the solvent tank and then *cannabis* plant matter solvent slurry is circulated through at least a solvent pump and the solvent tank, at which point *cannabis* plant matter solvent slurry is directed into a filter vessel that separates the *cannabis* plant matter from the cannabinoid enriched solvent. In this instance the filter vessel is the hopper.

The low volume high flow rate system depicted in FIG. 5 will preferably be built using pipes P1, P3, P3, a hopper H, and a solvent tank ST that are capable of withstanding pressure and that will not collapse when exposed to vacuum.

Embodiments of the invention may also be built on one or more vehicles. In such embodiments, for example, the hopper, the solvent pump, and pipes may reside on one vehicle and the solvent tank may reside on a second vehicle.

A hopper cover is any opening or door in the hopper wherein *cannabis* plant matter is introduced into the hopper. The invention is not limited to introducing *can-*

*nabis* plant matter through the hopper, *cannabis* plant matter may be introduced into the cannabinoid extraction apparatus through an opening In the apparatus other than the hopper.

An apparatus consistent with the invention has the ability to control the movement of liquid, vapor, or gas when performing an extraction of cannabinoids from *cannabis* plant matter. This movement may be controlled by an operator, by a control system, by an electronic control system, or by a combination thereof.

Examples of controlled fluid communication include yet are not limited to: The use of a vacuum pump to fill the hopper and pipes: The use of solvent pumps to move solvent: The use of valves to direct the flow of solvent or *cannabis* plant matter solvent slurry: Closing a valve or turning off a pump when soaking *cannabis* plant matter. The use of vacuum pumps and valves isolating the hopper when drying *cannabis* plant matter: a multi-position valve in communication with the hopper that allows a *cannabis* plant matter solvent slurry to flow without restriction in one orientation yet separates *cannabis* plant matter from cannabinoid enriched solvent using a filter or screen in another orientation. Embodiments of the invention also include instances where solvent is input into the hopper and is output from the hopper using the same pipe.

BRIEF DESCRIPTION OF THE DRAWINGS

FIG. 1 shows an embodiment of the invention, a mobile extractor in semi cross section.

FIG. 2 shows an embodiment of the invention, a mobile extractor mounted on a truck.

FIG. 3 shows an embodiment of the invention where the hopper is configured for dumping.

FIG. 4 shows an embodiment of the invention that supports a high flow rate of solvent or slurry of *cannabis* plant matter and solvent.

FIG. 5 shows another embodiment of the invention that supports high flow rates of solvent or slurry of *cannabis* plant matter solvent using a low volume of solvent to perform an extraction.

REFERENCES

[1] Journal of Chromatography 8,877 (2009) 4115-4124: "Innovative development and validation of an HPLC/DAD method for the qualitative determination of major cannabinoids in *cannabis* plant material": Benjamin De Backer et al.

[2] U.S. Pat. No. 6,365,416 B1: "Method of Preparing Δ9-THC", Elsohly et al. publication date Oct. 26, 1998.

[3] U.S. Pat. No. 6,730,519: "Method of Preparing Δ9-THC", Elsohly et al. publication date Jul. 4, 2002.

[4] Patent Application Publication US 2002/0039795 A1 "Method of Preparing Δ9-THC", Elsohly et al. patent date Apr. 2, 2002.

[5] U.S. Pat. No. 7,524,881 B2: "Production of Δ9-THC", Goodwin et al. patent date Apr. 28, 2009.

[6] U.S. Pat. No. 7,592,468 B2: "Production of Δ9-THC", Goodwin et al. patent date Sep. 22, 2009.

[7] U.S. Pat. No. 7,344,736 B2 "Extraction of Pharmaceutically Active Materials From Plant Material" by Whittle et al, patent date Mar. 18, 2008.

[8] US Patent Application Publication US 2008/0167483 A1 "Extraction of Pharmaceutically Active Materials From Plant Material" by Whittle et al publication date Jul. 10, 2008.

[9] U.S. Pat. No. 7,622,140 B2 "Process and Apparatus for Extraction of Active Substances and Enriched Extracts from Natural Products" by Whittle et al, patent date Nov. 24. 2009.

[10] US Patent Application Publication 2010/0119606 A1 "Process and Apparatus for Extraction of Active Substances and Enriched Extracts from Natural Products" by Whittle et al, published May 13, 2010.

[11] US Patent Application Publication US 2003/0017216A1 [11] by Schmidt et al entitled "Isolation of Herbal and Cannabinoid Medicinal Extracts", published Jan. 23, 2003.

The invention claimed is:

1. An apparatus for extracting cannabinoids from *cannabis* plant matter comprising:
   a solvent tank,
   liquid solvent, wherein the liquid solvent is initially contained within the solvent tank,
   a hopper,
   a secondary vessel,
   one or more valves,
   a first pump of one or more pumps that moves at least some portion of the liquid solvent from the solvent tank to the hopper, the liquid solvent contacting *cannabis* plant matter in the hopper creating a cannabinoid containing eluate in the at least some portion of the liquid solvent, wherein:
      the first pump of the one or more pumps is a vacuum pump that also removes at least a portion of oxygen from the hopper, wherein a first hose connects the vacuum pump to a top of the hopper, a second hose connects the vacuum pump a bottom of the hopper, and a third hose connects the vacuum pump to the solvent tank, and
   a gas other than oxygen that moves through a first valve of the one or more valves replacing the at least a portion of oxygen, and
   a first pipe of one or more pipes through which at least a portion of the eluate from the hopper is moved to the secondary vessel.

2. The apparatus of claim 1, wherein the vacuum pump primes a solvent pump of the one or more pumps.

3. The apparatus of claim 1, further comprising a sonic transducer generating sonic waves, wherein the sonic waves travel through the liquid solvent and into the said *cannabis* plant matter.

4. The apparatus of claim 1 further comprising an electronic control system.

5. The apparatus of claim 1, further comprising an ultrasonic transducer generating ultrasonic waves, wherein the ultrasonic waves travel through the liquid solvent and into the *cannabis* plant matter.

6. The apparatus of claim 1, further comprising a solvent pump of the one or more pumps that pumps a flow of the eluate from an output at the hopper to an input at the hopper.

7. The apparatus of claim 1, further comprising a second pump of the one or more pumps, wherein the second pump pumps the *cannabis* plant matter and the at least a portion of the eluate to the secondary vessel.

8. The apparatus of claim 7, wherein the secondary vessel is a filter vessel that separates the *cannabis* plant matter from the at least a portion of eluate.

9. The apparatus of claim 8, further comprising a second solvent tank, wherein the at least a portion of the eluate flows from the filter vessel and into the second solvent tank.

10. The apparatus of claim 1, wherein at least one of the one or more valves is controlled by a manual control.

11. The apparatus of claim 1, wherein at least one of the one or more valves directs a flow of liquid solvent from the solvent tank to the hopper.

12. The apparatus of claim 6, wherein the solvent pump pumps *cannabis* plant matter and the at least a portion of the eluate from the output at the hopper to the input at the hopper.

13. The apparatus of claim 1, further comprising a source of the gas other than oxygen, wherein the gas other than oxygen moves from the source of the gas to the hopper replacing the at least portion of oxygen.

14. The apparatus of claim 1, wherein a solvent pump of the one or more pumps also moves the liquid solvent from the solvent tank to the hopper.

15. The apparatus of claim 1, further comprising a vehicle, wherein the hopper is mounted on the vehicle.

16. The apparatus of claim 7, further comprising a solvent trap.

17. The apparatus of claim 16, wherein the solvent trap is a Woulff bottle.

* * * * *